US United States Patent [19]

Doorakian et al.

[11] 4,131,633
[45] Dec. 26, 1978

[54] LATENT CATALYSTS FOR PROMOTING REACTION OF EPOXIDES WITH PHENOLS AND/OR CARBOXYLIC ACIDS

[75] Inventors: George A. Doorakian, Bedford, Mass.; Dennis L. Schmidt, Houston, Tex.; Martin C. Cornell, III, São Paulo, Brazil

[73] Assignee: The Dow Chemical Company, Midland, Mich.

[21] Appl. No.: 786,314

[22] Filed: Apr. 11, 1977

Related U.S. Application Data

[60] Division of Ser. No. 650,212, Jan. 19, 1976, Pat. No. 4,048,141, which is a continuation-in-part of Ser. No. 629,345, Nov. 6, 1975, abandoned, which is a continuation of Ser. No. 417,844, Nov. 21, 1973, abandoned, which is a continuation-in-part of Ser. No. 290,891, Sep. 21, 1972, abandoned.

[51] Int. Cl.$^2$ .................. C08L 63/02; C08L 63/00
[52] U.S. Cl. .................. 260/837 R; 252/182; 252/188.3 R; 260/18 EP; 260/346.11; 260/347.91; 260/606.5 F; 260/606.5 P; 260/836; 560/209; 560/221; 560/224; 568/607; 528/89; 528/112; 528/366

[58] Field of Search ............ 260/2 EC, 2 BP, 47 EC, 260/47 EP, 47 EA, 49, 59 EP, 78.4 EP, 836, 837 R; 560/209; 252/188.3 R

[56] References Cited

U.S. PATENT DOCUMENTS

| 3,400,098 | 9/1968 | Parry et al. ..................... 260/47 |
| 3,477,990 | 11/1969 | Dante et al. ..................... 260/47 |
| 3,547,885 | 12/1970 | Dante et al. ..................... 260/47 |

FOREIGN PATENT DOCUMENTS

| 893191 | 2/1972 | Canada. |
| 2206218 | 8/1973 | Fed. Rep. of Germany. |

OTHER PUBLICATIONS

Chem. Abstracts, vol. 72, 4/13/70, p. 349 (90052g).

*Primary Examiner*—Theodore E. Pertilla
*Attorney, Agent, or Firm*—L. Wayne White

[57] ABSTRACT

Certain phosphorus-containing compounds are described herein which are novel latent catalysts for promoting the reaction between vicinal epoxides and phenols and/or carboxylic acids (or anhydrides). Precatalyzed epoxy resins are easily prepared using such catalysts.

16 Claims, No Drawings

LATENT CATALYSTS FOR PROMOTING REACTION OF EPOXIDES WITH PHENOLS AND/OR CARBOXYLIC ACIDS

CROSS-REFERENCE TO RELATED APPLICATIONS

This is a division of Ser. No. 650,212 filed Jan. 19, 1976, now U.S. Pat. No. 4,048,141, which in turn is a continuation-in-part application of Ser. No. 629,345 filed Nov. 6, 1975 abandoned, which in turn is a continuation of Ser. No. 417,844 filed on Nov. 21, 1973 abandoned, which in turn is a continuation-in-part of Ser. No. 290,891 filed Sept. 21, 1972 abandoned. The disclosure of each of these applications is incorporated herein by reference.

BACKGROUND OF THE INVENTION

1. Field of the Invention

This invention pertains to novel latent catalysts for promoting reaction between vicinal epoxides and phenols and/or carboxylic acids (or anhydrides of such acids). Such reactions are commercially important in that functional monomers (e.g. hydroxyethyl acrylate), hydraulic fluids (e.g. 2-phenoxyethanol) and high molecular weight linear or cross-linked epoxy resins are thus produced.

2. Description of the Prior Art

The reactions between epoxides and phenols and/or carboxylic acids (or anhydrides) have been extensively studied and many patents have been issued which describe these well known classes of reactants. See, for example, U.S. Patents:

U.S. Pat. No. 2,216,099
U.S. Pat. No. 2,633,458
U.S. Pat. No. 2,658,885
U.S. Pat. No. 3,377,406
U.S. Pat. No. 3,477,990
U.S. Pat. No. 3,547,881
U.S. Pat. No. 3,547,885
U.S. Pat. No. 3,694,407
U.S. Pat. No. 3,738,862

Canadian Pat. No. 893,191, German Pat. Nos. DT 2,206,281, and 2,335,199, and the text "Handbook of Epoxy Resins" by H. Lee and K. Neville, McGraw Hill, N.Y. (1967).

In addition to describing the classes of reactants, the above patents also show that (1) a catalyst is required to attain a satisfactory reaction rate and (2) those skilled in the art recognize that the reaction between epoxides and phenols is not, mechanistically speaking, the same as the reaction between epoxides and carboxylic acids (or anhydrides) due to the differences in products. The latter point is illustrated by the fact that substantially linear polymers are produced (U.S. Pat. No. 3,477,990) by reacting epoxy resins with polyfunctional phenols in the presence of a catalyst; whereas, cross-linked polymers are produced (U.S. Pat. No. 3,547,885) by reacting the same epoxy resins with a polycarboxylic acid (or anhydride) in the presence of the same catalysts. The reactive species which catalyze the reaction is therefore believed to be different in each instance. Thus, compounds which catalyze one reaction would not necessarily be expected to catalyze the other.

Several problems have been encountered in using many of the prior art catalysts. In many instances, the catalysts react with the epoxy reactant and thus preclude the option of marketing a blend comprising an epoxy resin and a catalyst; this blend is commonly referred to as a "precatalyzed epoxy resin". In other instances, the problem associated with the prior art catalysts is selectively; i.e. the catalysts simultaneously promote the reaction between the epoxy reactant and the phenolic hydroxyl group (or acid group) on the reactant and the aliphatic hydroxyl group(s) on the product giving branched or cross-linked polymers rather than the desired linear polymers. In still other instances, the reaction rate is unsatisfactory, and/or the product is highly colored and therefore unsatisfactory for many uses, and/or the product was contaminated with corrosive anions (e.g. chloride) and is therefore unacceptable for electrical encapsulation (potting). These and other problems have now been solved by the subject invention.

SUMMARY OF THE INVENTION

It has now been discovered that phosphorus-containing compounds corresponding to formula I–VII below are novel latent catalysts for promoting the reaction between vicinal epoxides and phenols and/or carboxylic acids (or anhydrides).

The novel catalysts are surprisingly effective in selectively catalyzing the desired reaction between the reactants at a suitable reaction rate. The reaction products are obtained in high yields and are of generally excellent color.

Additionally, the novel catalysts are surprisingly unreactive with epoxy resins at conventional storage temperatures. As a result, precatalyzed epoxy resins can now be produced by merely blending the subject catalysts with the epoxy resins. Such precatalyzed epoxy resins are, of course, novel compositions of matter.

THE NOVEL CATALYSTS

The phosphorus-containing compounds which we have found to be useful as latent catalysts are represented by formulas I–VII below:

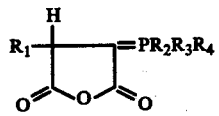   I

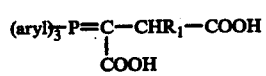   II

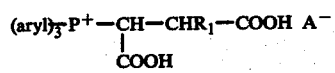   III

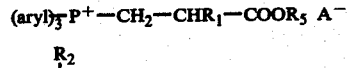   IV

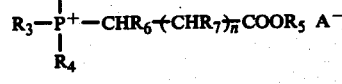   V

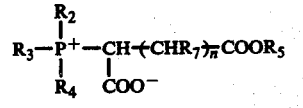   VI

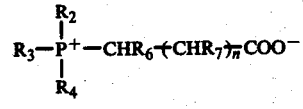   VII

In each of the above formulas:

$R_1$ is hydrogen or hydrocarbyl and is preferably hydrogen.

$R_2$–$R_4$ are hydrocarbyl groups, with the proviso that $R_2$–$R_4$ are not each aryl and formula VII. $R_2$–$R_4$ are preferably each alkyl and are most preferably each n-butyl.

$R_5$ is hydrogen or alkyl and is preferably hydrogen.

$R_6$ is hydrogen, alkyl, carboxy, or alkoxy carbonyl (—C(O)O-alkyl). $R_6$ is preferably hydrogen or carboxy and is most preferably hydrogen.

$R_7$ is hydrogen or hydrocarbyl and is preferably hydrogen.

"n" is from 0 to about 20 and is preferably 0, 1 or 2, and is most preferably 0 or 1.

$A^\ominus$ is a compatible anion (such as chloride, bromide, iodide, bisulfate, fluorosulfonate, acetate, diacetate, trifluoromethylsulfonate, etc.). The non-nucleophilic anions (such as bisulfate, acetate, diacetate, etc.) are the preferred anions when a latent catalyst is desired, as for example, in the preparation of precatalyzed epoxy resins.

Compounds represented by I are 3-hydrocarbylphosphoranylidene dihydro-2,5-furandiones which are a novel class of compounds. These compounds are conveniently prepared by contacting a trihydrocarbyl phosphine with maleic anhydride or an inertly-substituted derivative thereof (e.g. 2-methyl or 2-phenyl maleic anhydride, and the like). Representative examples of such compounds include 3-trialkyl-, 3-triaryl-, 3-trialkaryl-, 3-triaralkyl-, 3-tricycloalkyl- and 3-trialkenyl phosphoranylidene dihydro-2,5-furandiones and the like which typically have a total carbon content of up to about 60 carbon atoms (preferably from 7 to about 20 carbon atoms). 3-Triphenylphosphoranylidene dihydro-2,5-furandione is a known compound but the remaining members of I are thought to be novel compounds.

Compounds of II are conveniently prepared by hydrolyzing the corresponding compound from formula I with water.

Compounds of formula III are prepared by mixing the corresponding compound from formula II with an aqueous Bronsted acid (such as aqueous HCl, HBr, HI, $H_2SO_4$, acetic acid, trifluoroacetic acid, etc). Compounds of formula III are also prepared by reacting 2-chlorosuccinic acid (or anhydride) with the corresponding trihydrocarbyl phosphine.

Compounds of formula IV are conveniently prepared by warming the corresponding compound from III to a temperature sufficient to decarboxylate III (as evidenced by the liberation of gaseous carbon dioxide). Compounds of formula IV are also prepared by reacting omega-chloro (or bromo) propionic acid with the corresponding trihydrocarbyl phosphine. In each of these preparations, $R_5$ is, of course, hydrogen. The alkyl esters of such carboxylic acids can subsequently be prepared by conventional techniques.

Compounds of formula V can be prepared by reacting the appropriate phosphine with a chloro or bromo-substituted carboxylic acid or ester.

Compounds of formula VI can likewise be prepared by reacting the appropriate phosphine with a chloro- or bromo-substituted dicarboxylic acid or ester followed by treatment with base. Alternatively, compounds of formula VI can be prepared by reacting compounds of formula I, wherein $R_2$, $R_3$, $R_4$ are not all phenyl groups, with water.

Compounds of VII can be prepared by heating the corresponding compound of formula IV to cause decarboxylation (as evidence by the liberation of gaseous carbon dioxide). Alternatively, compounds of formula VII can be prepared by reacting the appropriate phosphine with a chloro- or bromo-substituted carboxylic acid followed by treatment with a base.

Illustrative examples of the instant class of novel catalysts include: 3-trimethyl-, 3-triethyl-, 3-tri(n-butyl)-, 3-trihexyl-, 3-tridecyl-, 3-tridodecyl-, 3-trioctadecyl-, 3-di(n-butyl)-3-hexyl-, 3-triphenyl-, 3-tri(methylphenyl)-, 3-tri(butylphenyl)-, 3-tri(octylphenyl)-, 3-tri(benzyl)-, 3-tri(phenethyl)-, 3-tri(phenylbutyl)-, 3-tri(3,5-dimethylbenzyl)-, 3-tricyclohexyl-, 3-triallyl-, 3-tricyclohexenylphosphoranylidene dihydro-2,5-furandione and the corresponding compounds bearing a hydrocarbyl substituent in the 4-position such as 4-methyl-, 4-phenyl, etc. and the like, and the corresponding hydrolyzed derivatives of the above compounds which upon hydrolysis, acidification and/or decarboxylation correspond to formulas II–VII. Other representative examples include the reaction products of tri-n-butylphosphine with chloroacetic acid, omega-chlorobutyric acid, omega-chlorohexanoic acid, omega-chlorododecanoic acid, omega-bromooctadecanoic acid, and the like, and the corresponding phosphobetaines and other like compounds. Mixtures of such compounds can also be used as catalysts.

The 3-triphenyl- and 3-tri (lower alkyl of 1–6 carbon atoms) phosphoranylidene dihydro-2,5-furandiones and the hydrolyzed derivatives thereof corresponding to formulas II–VI wherein: $R_1$ is hydrogen, $R_2$–$R_4$ are phenyl or lower alkyl or 1 to 6 carbon atoms; $R_5$ is hydrogen; $R_6$ is hydrogen or carboxy; $R_7$ is hydrogen; and $A^-$ is a compatible anion (e.g. chloro or bromo); and n is 2. Another class of preferred catalysts are those corresponding to formulas V–VII wherein: $R_2$–$R_4$ are alkyl of 1 to 6 carbon atoms (particularly n-butyl); $R_5$ is hydrogen; $R_6$ is hydrogen or carboxy; $A^\ominus$ is a compatible anion (e.g. chloride or bromide); and n is 0. The most preferred catalyst are 3-triphenylphosphoranylidene- and 3-tri(n-butyl)phosphoranylidene-dihydro-2,5-furandiones and the hydrolyzed derivatives thereof corresponding to formulas II–VII and, the compounds corresponding to formula V and VII wherein: $R_2$–$R_4$ are each n-butyl; $R_5$ and $R_6$ are each hydrogen; n is 0 and $A^-$ is a compatible anion (e.g. chloride or bromide).

In certain applications (e.g. coating of metal substrates with high molecular weight epoxy resins produced in accord with the instant invention) the presence of an anion $A^-$ may be undesirable. Chloride ion for example is known to be corrosive. In those instances, compounds of formulas I, II, VI and VII will have an advantage over the compounds represented by formulas III, IV, and V.

The above compounds are particularly useful in catalyzing the reaction between vicinal epoxides and phenols and/or carboxylic acids. In this utility, the amount used can be varied over a wide range. Genrally, however, they are used in a small but catalytic amount, as for example in amounts of from about 0.001 to about 10 percent by weight, based on the combined weight of reactants. Preferably, the catalyst is included in amounts of from about 0.05 to about 5 percent by weight.

THE EPOXY REACTANTS

As stated above, the reactants here used are well known classes of compounds.

The vicinal epoxides, for example, are organic compounds bearing one or more

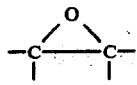

groups. The alkylene oxides of from 2 to about 24 carbon atoms, the epihalohydrins and the epoxy resins are perhaps the best known and most widely used members of the genus. Ethylene oxide, 1,2-propylene oxide, 1,2-butylene oxide and epichlorohydrin are the preferred monoepoxides. There are two preferred subclasses of epoxy resins. The first subclass corresponds to the general formula

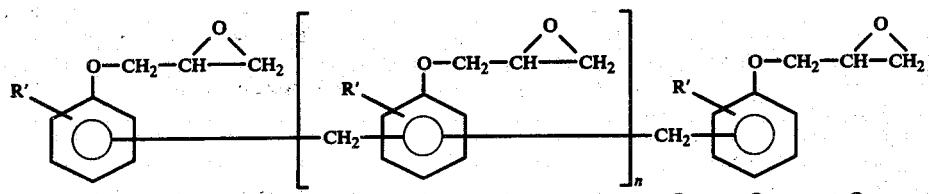

wherein R' is hydrogen or an alkyl radical and n is from about 0.1 to about 10, preferably from about 1 to about 2. Preparation of these polyepoxides is illustrated in U.S. Pat. No. 2,216,099 and U.S. Pat. No. 2,658,885. The second subclass corresponds to the general formula

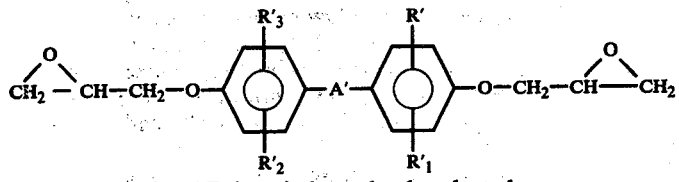

wherein R', $R_1'$, $R_2'$ and $R_3'$ are independently selected from hydrogen, bromine and chlorine and wherein A' is an alkylene (e.g. methylene) or alkylidene (e.g. isopropylidene) group having from about 1 to about 4 carbon atoms, or A' is a divalent radical of the formulas

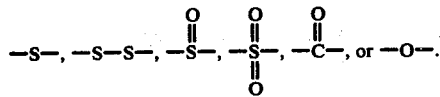

THE PHENOLIC REACTANTS

The phenols are organic compounds having one or more hydroxyl groups attached to an aromatic nucleus. This class of compounds therefore includes phenol, alpha and beta-naphthol, o-, m-, or p-chlorophenol, alkylated derivatives of phenol (e.g. o-methyl-, 3,5-dimethyl-, p-t-butyl- and p-nonylphenol) and other monohydric phenols as well as polyhydric phenols, such as resorcinol, hydroquinone, etc. The polyhydric phenols bearing from 2 to 6 hydroxyl groups and having from 6 to about 30 carbon atoms are particularly useful in the reaction with epoxy resins to form high molecular weight resins (linear or cross-linked) useful in coatings.

Particularly preferred polyhydric phenols are those corresponding to the formula

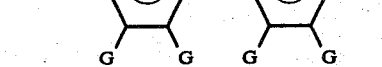

wherein G is hydrogen, halogen (fluoro, chloro or bromo) or hydrocarbyl and X is oxygen, sulfur, —SO—, —SO$_2$—, bivalent hydrocarbon radicals containing up to 10 carbon atoms, and oxygen-, sulfur- and nitrogen-containing hydrocarbon radicals, such as —OR"O—, —OR"OR"O—, —S—R"—S—, —S—R'λ'—S—R"—S—, —OSiO—, —OSiOSiO—,

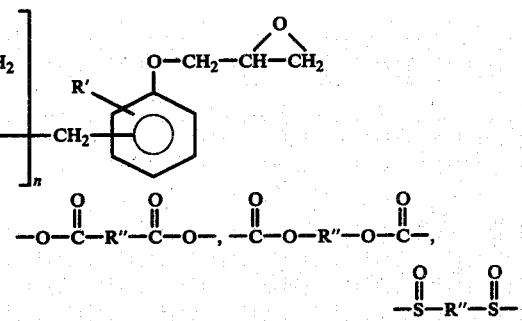

and —SO$_2$—R"—SO$_2$— radicals wherein R" is a bivalent hydrocarbon radical. 4,4'-Isopropylidenediphenol (i.e. bisphenol-A) is the most preferred phenol.

THE CARBOXYLIC ACID REACTANTS

The organic carboxylic acids and anhydrides are likewise well known. The acids bear one or more carboxyl groups on the organic nucleus. The anhydrides are prepared from such carboxylic acids by the removal of water therefrom in an intra- or intermolecular condensation. This class of compounds therefore includes acetic, propionic, octanoic, stearic, acrylic, methacrylic, oleic, benzoic, phthalic, isophthalic, maleic, succinic, adipic, itaconic, polyacrylic an polymethacrylic acids, and the like, and anhydrides thereof, such as acetic anhydride, phthalic anhydride, hexahydrophthalic anhydride, etc.

There are two subclasses of carboxylic acids and anhydrides that are particularly important based on their reaction with epoxy resins. The reaction of ethylenically unsaturated monocarboxylic acids with epoxy resins produces hydroxy-substituted esters or polyesters which are particularly useful in the preparation of coatings, adhesives, etc. See, for example, U.S. Pat. No.

3,377,406. Acrylic and methacrylic acid are particularly useful in this regard. Accordingly, the ethylenically unsaturated monocarboxylic acids are a preferred subclass of acids.

The second preferred subclass of acids is comprised of members which are useful in cross-linking expoxy resins. The members of this subclass are normally di- or tribasic acids, or anhydrides thereof, and are preferably liquid or low-melting solids such as succinic, maleic, or hexahydrophthalic acids or anhydrides and the like. Other such acids and anhydrides are shown, for example, in U.S. Pat. Nos. 2,970,983 and 3,547,885.

RATIO OF REACTANTS

The ratio of vicinal epoxide reactant to phenol and/or carboxylic acid reactant in the subject process can vary over a wide range depending upon the product desired. E.g. if a product terminated with a phenolic ether group is desired, obviously one would employ an excess of phenol in the process, etc.

SOLVENTS

In many instances the reactants are liquid and no solvent or diluent is needed. In other cases, however, where one or both of the reactants are solid or viscous liquids, an inert solvent or diluent can be used advantageously. Suitable such inert solvents or diluents are known to those skilled in the art and include ketones (such as acetone, methyl ethyl ketone, etc.), hydrocarbons (such as benzene, toluene, xylene, cyclohexane, ligroin, etc.) and the like.

OTHER PROCESS PARAMETERS

Generally, the reaction mixture is warmed at temperatures in the range of from about 50° C. to about 225° C. (preferably 100°–175° C.) until an exotherm begins and, after the exotherm has peaked, substantially warmed in the same range for an additional time to assure substantially complete reaction. Atmospheric or superatomspheric pressures (e.g. up to about 200 psig) are common.

THE REACTION PRODUCTS

The products here produced are generally known compounds in industry. The particular product produced will vary in properties depending upon the selection and ratio of reactants used in the process. Every combination of reactants, of course, need not be discussed but the following discussion will illustrate the types of products which can be produced.

The reaction products here produced by reacting an epoxy resin with a phenol in the presence of the subject catalysts are phenolic ethers bearing one or more aliphatic secondary hydroxyl groups. Such aliphatic hydroxyl groups are formed in the ring-opening reaction between the oxirane and phenolic hydroxyl groups. Additionally, the reaction products bear a terminal epoxy group(s) or a phenolic hydroxyl group(s) depending upon the ratio of reactants. Consequently, they are reactive intermediates which can be cured (cross-linked) with many polyfunctional curing agents to form hard, insoluble solids which are useful coatings. A listing of several known curing agents which are suitable for use herein is found in U.S. Pat. No. 3,477,990. The cured products (particularly those of high molecular weight) are useful as surface coatings, as adhesive layers in laminates, coatings on filament windings, in structural binding applications, and the like. The reaction products prepared from halogenated (particularly brominated) phenols are particularly useful in flameproofing applications since they tend to be self-extinguishing. Thus, they are useful in forming cured coatings for wood paneling and as adhesive layers in wood laminates, etc.

The reaction products here produced by reacting an epoxy resin with a monocarboxylic acid (or anhydride of such acids) have terminal ester groups and are useful in coatings, adhesives, reinforced plastics, moldings, etc. The reaction products formed by reacting epoxy resins with polycarboxylic acids, or anhydrides thereof, are cross-linked insoluble resins used in coatings, etc.

Functional monomers are here produced by reacting a $C_2$ to $C_4$ alkylene oxide with acrylic or methacrylic acid. Hydraulic fluids are here prepared by reacting lower alkylene oxide with a phenol in substantially equimolar amounts. Nonionic surfactants are here prepared by reacting an alkylated monohydric phenol with a $C_2$ to $C_4$ alkylene oxide, or mixture of such alkylene oxides.

Other useful products can be similarly prepared by the reaction of vicinal epoxides with phenols and/or carboxylic acids (or anhydrides) in the presence of the subject catalysts.

The following examples further illustrate the invention:

EXAMPLE 1

3-Tri-n-Butylphosphoranylidene Dihydro-2,5-furandione

Maleic anhydride (9.81 g; 0.1 mole) in 25 ml acetone and tri-n-butylphosphine (20.23 g; 0.1 mole) in acetone were blended at 0°–5° C. under a blanket of dry nitrogen. The resulting red solution was stirred for 1 hour at room temperature and then placed under vacuum to remove the bulk of the acetone solvent. The resulting red viscous liquid gave 15 g of yellow-brown crystalline product. This solid was separated by filtration and washed with cold acetone giving a yellow crystalline product which melts at 70° C., resolidifies and melts again at 85° C. with gassing. The infrared (IR) and nuclear magnetic resonance (NMR) spectra and elemental analysis of the product were consistent with a compound represented by the structure

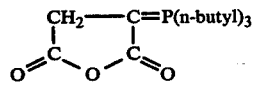

Calc. for $C_{16}H_{29}O_3P$: C 63.90; H 9.73; P 10.31. Found: C 63.51; H 10.15; P 10.16.

EXAMPLES 2–7

The compounds 3-triphenylphosphoranylidene and diphenylethylphosphoranylidene dihydro-2,5-furandiones; 3-tri-n-butylphosphoranylidene and 3-triphenylphosphoranylidene 4-methyl dihydro-2,5-furandiones; and 3-tri-n-butylphosphoranylidene and 3-triphenylphosphoranylidene 4-phenyl dihydro-2,5-furandiones were prepared in an analogous manner using the appropriate reactants.

EXAMPLE 8

2-Triphenylphosphoranylidene-1,4-butanedioic Acid

The title compound was prepared by stirring 3-triphenylphosphoranylidene dihydro-2,5-furandione (5.0 g, 0.014 mole) for 48 hours in 100 ml water. The solid residue was isolated by filtration and air-dried to give essentially quantitative yields of a product as a white crystalline solid whose IR spectrum and elemental analysis corresponded to the structure

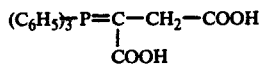

Calc. for $C_{22}H_{19}O_4P$: C 69.84; H 5.06; P 8.19. Found: C 69.86; H 5.16; P 8.18.

EXAMPLE 9

Tri-n-Butyl(1,2-dicarboxyethyl)phosphonium, Hydroxide, Inner Salt

Maleic anhydride (223 g; 2.28 moles) dissolved in 200 ml of acetone was added dropwise over 1.5 hours to a vigorously stirred solution of tri-n-butylphosphine (484 g; 2.28 moles) in 1 liter of acetone at ambient conditions. The burgundy-colored reaction mixture was stirred overnight with water (86.4 g; 4.80 moles) giving a pinkish-white crystalline solid which melts at 107°–108.5° C. with gassing, resolidifies and melts again at 175°–177° C. The IR and NMR spectra and elemental analysis data were consistant with a compound represented by the phosphobetaine structure

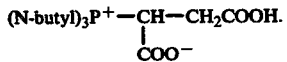

Calc. for $C_{16}H_{31}O_4P$: C 60.30; H 9.88; P 9.75. Found: C 60.40; H 9.93; P 10.00.

EXAMPLES 10–11

The 3-tri-n-butylphosphoranylidene 4-methyl and 4-phenyl dihydro-2,5-furandiones from Examples 4 and 6 were hydrolyzed by stirring in water to give compounds corresponding to the formula

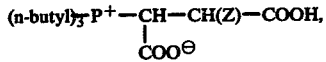

wherein Z is methyl and phenyl, respectively.

EXAMPLES 12–13

Triphenyl(1,2-dicarboxyethyl)phosphonium Halide

The title compounds were prepared by stirring 3-triphenylphosphoranylidene dihydro-2,5-furandione (from Example 2) and 2-triphenylphosphoranylidene-1,4-butanedioic acid (from Example 8) with an equimolar amount of aqueous HCl or HBr. The solid product was separated by filtration and dried under vacuum to give a water-soluble white crystalline solid. The IR and NMR spectra along with elemental analysis data were consistent with a compound corresponding to the structure

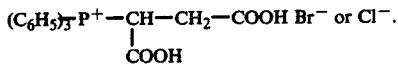

EXAMPLE 14

Tri-n-butyl(1,2-dicarboxyethyl)phosphonium Chloride

The title compound was prepared and identified by the procedures in Example 12 except that the furandione reactant here used was the tri-n-butylphosphoranylidene dihydro-2,5-furandione from Example 1 and HCl was used in place of HBr. It too was a water-soluble white crystalline solid.

EXAMPLE 15–17

Trihydrocarbyl(2-carboxyethyl)phosphonium Halides

Water-soluble white crystalline solid compounds corresponding to the formulas $(C_6H_5)_3P^+\text{-}CH_2CH_2COOH$ $A^-$ wherein $A^-$ is a bromide or chloride and $(n\text{-butyl})_3P^+\text{-}CH_2CH_2COOH$ $Cl^-$ were prepared by the warming compounds from Examples 12–14, respectively, until gassing occurred and maintaining them at that temperature until gassing ceased. The title compounds were identified by IR, NMR and elemental analysis data.

EXAMPLE 18

Tri-n-butyl(2-carboxyethyl)phosphonium, Hydroxide, Inner Salt

The title compound was prepared by warming the product from Example 9 overnight at 70° C. and 0.1 mm. Hg. The product was thus obtained as a white, hygroscopic crystalline solid melting at 175°–177° C. The IR, NMR and elemental analysis data were consistent with a compound corresponding to the formula $(n\text{-butyl})_3P^+\text{-}CH_2CH_2COO^-$.

Calc. for $C_{14}H_{31}O_2P$: C 65.66; H 11.39; P 11.29. Found: C 65.97; H 11.48; P 10.93.

EXAMPLE 19

Diethylphenyl(1,2-dicarboxyethyl)phosphonium, Hydroxide, Inner Salt

Maleic anhydride (3.63 g; 0.037 mole) and 12.5 ml of acetone was added dropwise over a 5 minute period with vigorous stirring to diethylphenylphosphine (6.15 g, 0.037 mole) in 12.5 ml of acetone. The reaction solution was stirred for an additional hour at ambient conditions after the addition was complete. Water (3.3 ml) was added to the reaction mixture causing a white precipitate. The precipitate was filtered and washed with acetone and air-dried. The infrared spectrum and elemental analysis of the compound were consistent with a compound corresponding to the formula

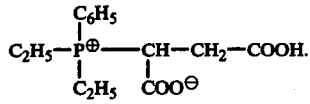

EXAMPLE 20

Preparation of Tri-n-butyl(1-carboxyethyl)phosphonium Chloride

Tri-n-butyl phosphine (20.27 g, 25 ml, 0.1 mole) was added dropwise to a rapidly stirred solution of 2-chloropropanoic acid (10.85 g, 9.1 ml, 0.1 mole) in 31 ml of acetone. The reaction was, of course, exothermic, and the addition of the phosphine was maintained at a rate such that the temperature did not exceed about 35° C.

After the addition was complete, the acetone solvent was removed under reduced pressure leaving a viscous liquid having an infrared spectrum and elemental analysis corresponding to the formula

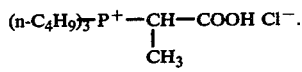

EXAMPLE 21

Preparation of Tri-n-butyl(carboxymethyl)phosphonium Chloride

Tri-n-butyl phosphine (4.04 g, 0.02 mole) was added dropwise to a rapidly stirred solution of monochloroacetic acid (1.85 g, 0.02 mole) and 3.2 ml of methanol. The addition of the phosphine was at a rate such that the reaction temperature did not exceed about 30° C. The methanol solvent was subsequently evaporated under reduced pressure leaving a colorless viscous liquid whose infrared spectrum and elemental analysis corresponded to a compound of the formula $(n-C_4H_9)_3P^{\oplus}-CH_2-COOH \ Cl^{\ominus}$.

EXAMPLE 22

Preparation of Tri-n-butyl(carboxymethyl)phosphonium, Hydroxide, Inner Salt

An aliquot from the product of Example 21 was dissolved in an equal volume of methanol and contacted with a commercial ion exchange resin in the hydroxide form. The resin was removed by filtration and the remaining liquid twice more contacted with fresh samples of the ion exchange resin. The liquid thus treated was condensed under reduced pressure leaving a colorless viscous liquid whose infrared spectrum and elemental analysis corresponded to a compound of the formula $(n-C_4H_9)_3P^+-CH_2-COO^-$.

EXAMPLE 23

Preparation of Tri-n-butyl(carboxypropyl)phosphonium Chloride

Tri-n-butyl phosphine (0.1 mole) and 4-chlorobutyric acid (0.1 mole) were refluxed in toluene for 4 hours. Evaporation of the solvent from the reaction mixture left a viscous liquid whose infrared spectrum and elemental analysis corresponded to a compound of the formula $(n-C_4H_9)_3P^+-(CH_2)_3COOH \ Cl^-$.

EXAMPLE 24

Preparation of Tri-n-butyl(3-carboxypropyl) phosphonium, Hydroxide, Inner Salt An aliquot of the product from Example 23 was dissolved in an equal volume of methanol and treated pursuant to Example 22. Upon removing the solvent there remained a colorless, viscous liquid whose infrared spectrum corresponded to a compound of the formula $(n-C_4H_9)_3P^+-(CH_2)_3COO^-$.

EXAMPLE 25

Preparation of the Ethyl Ester of Tri-n-butyl (carboxymethyl)phosphonium Chloride A solution of ethylchloroacetate (9.69 g. 0.079 mole) in methanol (12 g, 15.2 ml) was added dropwise to a solution of tri-n-butylphosphine (16.2 g, 0.083 mole) in methanol (13.0 g, 16.5 ml). A slight temperature exotherm was observed. Following the temperature exotherm, the reaction mixture was stirred at room temperature for 4 hours. The methanol solvent was subsequently evaporated under reduced pressure leaving the desired product as a colorless oil. The oil was triturated with ethyl ether to yield 18.0 g of a white solid melting at 78–80° C. The infrared spectrum and elemental analysis were consistent with a compound of the formula $(n-C_4H_9)_3P^+-CH_2-COO-C_2H_5 \ Cl^-$.

EXAMPLE 26

Preparation of the Ethyl Ester of Tri-n-butyl (2-carboxyethyl)phosphonium Chloride An equimolar mixture of tri-n-butyl phosphine and ethyl 3-chloropropionate were heated in refluxing toluene for 4 hours. The toluene was subsequently stripped from the reaction mixture leaving a colorless viscous oil. Analysis of the product was consistent with a compound of the formula $(n-C_4H_9)_3P^+-CH_2CH_2-COO-C_2H_5 \ Cl^-$.

LINEAR EPOXY RESINS

The following examples illustrate the effectiveness of the instant catalysts in promoting the reaction between epoxy resins and phenols to form substantially linear epoxy resins.

EXAMPLE 27

To a reaction vessel equipped with a stirring means and a temperature recording means was charged under a nitrogen purge 75.79 parts by weight of the diglycidyl ether of 4,4'-isopropylidenediphenol having an epoxy equivalent weight of 187, 24.21 parts of 4,4'-isopropylidenediphenol (bisphenol-A) and 0.15 parts of 3-triphenylphosphoranylidenedihydro-2,5-furandione,

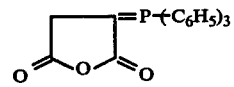

dissolved in about 5 ml of methanol. The stirred reaction mixture was warmed from ambient temperature to about 150° C. at a rate of 3° C./minute. At 150° C. the heat was turned off but the reaction continued to exotherm to a peak temperature of about 212° C. After the exotherm subsided, the mixture was heated at 150° C. for an additional 2.5 hours. Theoretical epoxide content = 8.20%. Observed = 8.16%. A linear epoxy resin was thus produced having excellent color.

EXAMPLES 28–29

In like manner a mixture of 0.0936 parts by weight of 3-tri-n-butylphosphoranylidenedihydro-2,5-furandione, 75.79 parts of the diglycidyl ether of bisphenol A (EEW 187) and 24.21 parts of bisphenol A was warmed to 150° C. The exotherm peaked at about 216° C. and the resulting product was warmed for 5 hours at 160° C. A linear epoxy resin was thus produced. Theoretical epoxide content = 8.00%. Observed = 7.57%.

A product with similar properties was produced in an identical run except that 4-phenyl-3-(tri-n-butylphosphoranylidene)dihydro-2,5-furandione (0.0994 parts) was used as the catalyst. Theoretical epoxide content = 8.00%. Observed = 7.75%.

EXAMPLES 30–31

In like manner, a mixture of 0.1338 parts by weight of 4-phenyl-3-(triphenylphosphoranylidene)dihydro-2,5-furandione, 75.79 parts of the diglycidyl ether of bisphenol-A (EEW 187) and 24.21 parts of bisphenol-A was warmed to 150° C. The exotherm peaked at 213° C. and the resulting product was warmed 2 hours at 160° C. A linear epoxy resin was obtained. Theoretical epoxide content = 8.00%. Observed = 8.03%.

A product with similar properties was produced in an identical run except that 4-methyl-3-(tri-n-butylphosphoranylidene)dihydro-2,5-furandione (0.0966 parts) was used as the catalyst. Theoretical epoxide content = 8.00%. Observed = 7.82%.

EXAMPLES 32–41

In like manner, the compounds from example 9, 12, 16, 20, 21, 22, 23, 24, 25 and 26 were observed to be effective catalysts for promoting the reaction between the epoxy resin and bisphenol-A used in Examples 27–31 above under similar conditions. The products of Example 9, 18, 21 and 22 were particularly effective in forming linear epoxy resins of very high molecular weight by the aforementioned reaction using the appropriate ratios of reactants.

Each of the linear epoxy resins produced above had good color. They are curable (cross-linkable) with conventional curing agents, such as dicyandiamide, polyamines, anhydrides, etc. The cured resins are tough solvent-resistant materials which are useful as coatings.

Branched and/or cross-linked products are similarly prepared in the instant process by (1) reacting an epoxy resin having at least 3 epoxy groups per molecule with a phenol having at least 2 hydroxyl groups, or (2) by reacting an epoxy resin having at least 2 epoxy groups per molecule with a phenol having at least 3 hydroxyl groups in the presence of the subject catalysts. Such branched and/or cross-linked products are likewise useful as coatings.

CROSS-LINKED EPOXY RESINS

The following examples illustrate the effectiveness of the instant catalysts in promoting the reaction between epoxy resins and organic carboxylic acids (or anhydrides) to form cross-linked resins having excellent physical properties.

EXAMPLES 34–38

The compounds from Examples 2, 8, 9, 18, 19, 21, 22 and 25 were separately added at a 0.15 weight percent catalyst concentration to aliquots of a mixture consisting of a liquid epoxy resin (100 parts by weight) having an EEW of 172–176 and hexahydrophthalic anhydride (80 parts by weight). The catalyzed mixtures were formed by preheating the epoxy resin and anhydride components in separate containers to 70° C. and then blending such components and the particular catalyst with efficient stirring. The catalyzed mixtures were degassed under vacuum. Gel times were measured in aliquots of each of the catalyzed mixtures at 110° C. and varied from about 1 to about 2.25 hours. The remainder of the catalyzed mixtures were poured into separate molds and heated two hours at 110° C. and 2 hours at 150° C. thus producing a colorless, cross-linked sheet casting in each instance having excellent physical properties in terms of modulus, tensile and elongation (as determined by ASTM D-638-68) and flexural strength (as determined by ASTM D-790). These cross-linked materials would likewise be extremely useful as coatings.

Other species of the instant catalysts can be similarly used. In addition, the above anhydride can be replaced with other anhydrides of organic carboxylic or polycarboxylic acids as defined above. For example, maleic anhydride could be used in the above reaction leading to cross-linked products. Alternatively, acrylic or methacrylic acid could be used in the above reaction leading to epoxy resins termined with a free-radical or thermally polymerizable vinyl groups. Such compounds are likewise useful coating material.

PRECATALYZED EPOXY RESINS

Precatalyzed epoxy resins were prepared by blending the diglycidyl ether of bisphenol-A (EEW 187) with the catalysts from Examples 1, 2, 4–9, 18, 21, 22 and 26. These mixtures were stored for up to 4–8 weeks at 50° C. and used in experiments otherwise identical to Examples 27–33 above. The stored mixtures showed little, if any, loss in reactivity and their reaction products with phenols had essentially the same properties as those obtained in Examples 27–33. Other species of the instant catalysts can be similarly used.

OXYALKYLATION OF PHENOLS

Phenol and ethylene oxide (1.05 to 1.1 mole/mole of phenol) where charged to a reaction vessel under sufficient pressure to maintain the reactants in substantially liquid phase at 150° C. To this was added 0.1 weight percent of the instant catalysts and the reaction mixture heated with stirring for 3–4 hours at 150° C. The reaction mixture was cooled and the volatiles removed under vacuum. The liquid residue was analyzed and the results are shown in Table I.

TABLE I

| Experiment | Product from | Product Composition (Wt.%) | | Conversion of Phenol (%) |
|---|---|---|---|---|
| | | $C_6H_5OCH_2CH_2OH$ | $C_6H_5O(CH_2CH_2O)_2H$ | |
| 1 | Ex. 2 | 92.0 | 4.1 | 97.1 |
| 2. | Ex. 8 | 85.4 | 6.4 | 88.1 |
| 3 | Ex. 9 | 85.2 | 8.7 | 95.3 |
| 4 | Ex. 15 | 86.9 | 7.3 | 95.9 |
| 5 | Ex. 18 | 89.9 | 6.7 | 97.6 |
| 6 | Ex. 19 | 94.4 | 4.6 | 99.5 |

Other species of the instant catalysts can be similarly used.

OXYALKYLATION OF ACIDS

Run 1: Acrylic acid (1.8 g; 0.025 mole); p-t-butylphenyl glycidyl ether (5.15 g; 0.025 mole) and 0.15 weight percent (10.4 milligrams) of tri-n-butyl(2-carboxyethyl)-phosphonium, hydroxide, inner salt, $(C_4H_9)_3P^{\oplus}$-$CH_2CH_2COO^{\ominus}$, were mixed in a reaction vessel and heated at 110°–120° C. for 5.5 hours. The extent of the reaction was measured by titration for unreacted acid and the product identified by IR analysis. The desired product, $C_4H_9$—$C_6H_4$—$OCH_2CH(OH)CH_2O$—$C(O)CH=CH_2$, was obtained in about 97 percent yield, based on theory. In a duplicate run, without catalyst, the ester was produced in only about 31 percent yield.

Run 2: Acrylic acid (3.605 g; 0.05 mole), t-butyl glycidyl ether (6.51 g; 0.05 mole) and 0.15 weight percent (15.2 milligrams) of tri-n-butyl(2-carboxyethyl)phosphonium, hydroxide, inner salt, were blended and heated at 80°–90° C. for 9 hours. The desired product, t—$C_4H_9OCH_2CH(OH)CH_2O$—$C(O)CH=CH_2$, was obtained in about 82 percent yield. In a duplicate run, without catalyst, the product was produced in only 48 percent yield. Similarly, other reactive monomers (e.g. 2-hydroxyethyl, 2-hydroxypropyl- and 2-hydroxybutylacrylate and methacrylate) can be prepared by condensing the appropriate vicinal alkylene oxide onto acrylic or methacrylic acid in the presence of the instant catalysts.

From the above, it is apparent that the instant catalysts are extremely effective in promoting the reaction between vicinal epoxides and phenols and/or organic carboxylic acids (or anhydrides). It is also apparent that the novel catalysts are latent catalysts at temperatures below about 50° C. and are, therefore, extremely useful in making precatalyzed epoxy resins.

We claim:

1. A composition comprising (a) an epoxide bearing at least one vicinal epoxy group per molecule; (b) (1) an organic carboxylic acid or anhydride of said acid or (2) a mixture of a phenol and an organic carboxylic acid or anhydride of said acid, and (c) a small but catalytic amount of phosphorus-containing catalyst corresponding to the formula

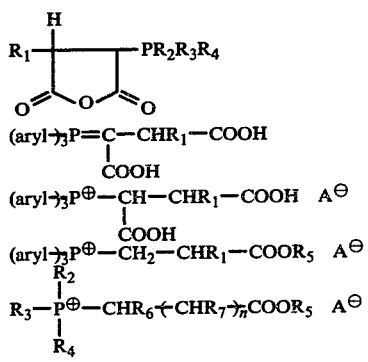

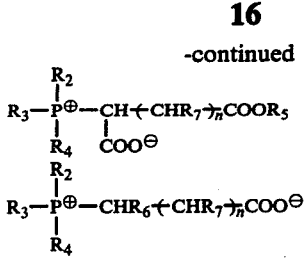

or a mixture thereof, wherein:
$R_1$ is hydrogen or hydrocarbyl,
$R_2$–$R_4$ are hydrocarbyl groups, with the proviso that $R_2$–$R_4$ are not each aryl in formula VII,
$R_5$ is hydrogen or alkyl,
$R_6$ is hydrogen, alkyl, carboxy, or alkoxy carbonyl,
$R_7$ is hydrogen or hydrocarbyl,
n is from 0 to about 20, and
$A^{\ominus}$ is a compatible anion.

2. The composition defined by claim 1 wherein (a) is an epoxy resin and (b) is (1) a polyhydric phenol of from 6 to about 30 carbon atoms bearing from 2 to 6 hydroxyl groups, (2) an ethylenically unsaturated monocarboxylic acid or anhydride thereof (3) a polybasic carboxylic acid, or anhydride thereof or any mixture thereof.

3. The composition defined by claim 1 wherein (a) is the diglycidyl ether of 4,4′-isopropylidenediphenol, and (c) is 3-triphenyl- or 3-tri-n-butylphosphoranylidene dihydro-2,5-furandione or a hydrolyzed derivative thereof and wherein (c) is present in an amount of from about 0.05 to about 5 percent by weight, based on the combined weights of (a) and (b).

4. The composition defined by claim 1 wherein (b) is an ethylenically unsaturated monocarboxylic acid or anhydride thereof.

5. The composition defined by claim 4 wherein (b) is acrylic or methacrylic acid.

6. The composition defined by claim 1 wherein (b) is a polybasic organic carboxylic acid or anhydride thereof.

7. The composition defined by claim 6 wherein (b) is succinic, maleic or hexahydrophthalic acid or anhydride.

8. The composition defined by claim 1 wherein (a) is an epoxy resin corresponding to the formula

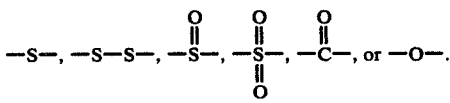

wherein R′, $R_1′$, $R_2′$ and $R_3′$ are independently selected from hydrogen, bromine and chlorine and wherein A′ is an alkylene or alkylidene group having from about 1 to about 4 carbon atoms, or A′ is a divalent radical of the formula $$-S-, \quad -S-S-, \quad -\overset{O}{\underset{}{S}}-, \quad -\overset{O}{\underset{O}{\overset{\|}{S}}}-, \quad -\overset{O}{\underset{}{C}}-, \text{ or } -O-.$$

9. The composition defined by claim 1 wherein (a) is an alkylene oxide of from 2 to 4 carbon atoms or a mixture thereof and (b) is acrylic acid or methacrylic acid.

10. The composition defined by claim 1 wherein (a) is an epoxy resin corresponding to the formula

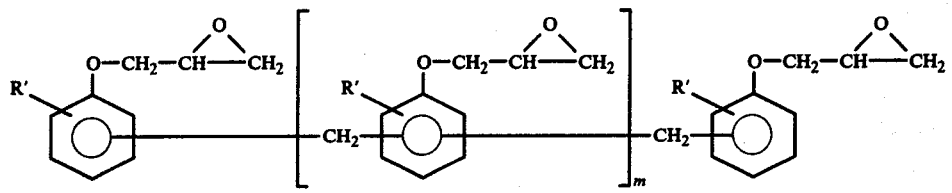

wherein R' is hydrogen or an alkyl radical and m is from about 0.1 to about 10.

11. The composition defined by claim 10 wherein m is from about 1 to about 2.

12. The composition defined by claim 1 wherein $R_1$ is hydrogen; $R_2$–$R_4$ are alkyl; $R_5$ is hydrogen; $R_6$ is hydrogen or carboxy; $R_7$ is hydrogen; and n is 0, 1 or 2.

13. The composition defined by claim 12 wherein $R_2$–$R_4$ are each n-butyl; $R_6$ is hydrogen; and n is 0 or 1.

14. The composition defined by claim 13 wherein (c) is 3-tri-n-butylphosphoranylidene dihydro-2,5-furandione; tri-n-butyl(1,2-dicarboxyethyl)phosphonium hydroxide, inner salt; a tri-n-butyl(2-carboxyethyl)phosphonium salt tri-n-butyl(2-carboxyethyl)phosphonium hydroxide, inner salt; a tri-n-butyl(carboxymethyl)phosphonium salt; or tri-n-butyl (carboxymethyl)phosphonium hydroxide, inner salt.

15. The composition defined by claim 1 wherein (c) is present in amounts of from about 0.001 to about 10 percent by weight, based on the combined weights of (a) and (b).

16. The composition defined by claim 15 wherein (c) is present in amounts of from about 0.05 to about 5 percent by weight, based on the combined weights of (a) and (b).

* * * * *

UNITED STATES PATENT AND TRADEMARK OFFICE
CERTIFICATE OF CORRECTION

PATENT NO. : 4,131,633
DATED : December 26, 1978
INVENTOR(S) : George A. Doorakian, Dennis L. Schmidt and Martin C. Cornell, III It is certified that error appears in the above-identified patent and that said Letters Patent are hereby corrected as shown below:

Column 1, line 44, delete "2,206,281" and insert -- 2,206,218 --.

Column 2, line 4, delete "selectively" and insert -- selectivity --.

Column 3, line 45, delete "trifluoracetic" and insert -- trifluoroacetic --.

Column 4, line 2, delete "IV" and insert -- VI --.

Column 6, lines 17 and 18, delete " -S-R'ג'-S-R"-S- " and insert -- , -S-R"-S-R"-S- --.

Column 6, lines 58 and 59, delete "an polymetharcrylic" and insert -- and polymethacrylic --.

Column 7, line 6, delete "expoxy" and insert -- epoxy --.

Column 7, lines 39 and 40, delete "superatomspheric" and insert -- superatmospheric --.

UNITED STATES PATENT AND TRADEMARK OFFICE
CERTIFICATE OF CORRECTION

PATENT NO. : 4,131,633
DATED : December 26, 1978
INVENTOR(S) : George A. Doorakian, Dennis L. Schmidt and Martin C. Cornell, III It is certified that error appears in the above-identified patent and that said Letters Patent are hereby corrected as shown below:

Column 13, line 28, delete "example" and insert
-- examples --.

Column 15, line 42, after "of" insert "a".

Signed and Sealed this

Eighth Day of May 1979

[SEAL]

Attest:

RUTH C. MASON
Attesting Officer

DONALD W. BANNER
Commissioner of Patents and Trademarks